United States Patent [19]

Cuthbertson et al.

[11] Patent Number: 4,934,177
[45] Date of Patent: Jun. 19, 1990

[54] SOLUTE CONCENTRATION MEASUREMENT APPARATUS

[75] Inventors: Robin C. Cuthbertson, East Lothian; Ian S. Forrest, Midlothian, both of Scotland

[73] Assignee: Scottish & Newcastle Breweries plc., Edinburgh, Scotland

[21] Appl. No.: 213,440

[22] Filed: Jun. 28, 1988

Related U.S. Application Data

[63] Continuation of Ser. No. 10,522, Feb. 3, 1987, abandoned.

[30] Foreign Application Priority Data

Feb. 4, 1986 [GB] United Kingdom ............... 8602687
Jul. 4, 1986 [GB] United Kingdom ............... 8616327

[51] Int. Cl.$^5$ ............................................. G01N 9/00
[52] U.S. Cl. ................................................. 73/32 A
[58] Field of Search ............. 73/589, 597, 32 R, 32 A, 73/590, 61.1 R; 99/277, 280, 285; 426/7, 11

[56] References Cited

U.S. PATENT DOCUMENTS

| | | | |
|---|---|---|---|
| 3,413,595 | 11/1968 | Babikov et al. | 73/597 |
| 3,973,430 | 8/1976 | Cirulis et al. | 73/597 |
| 4,235,099 | 11/1980 | Ishizaka | 73/32 A |
| 4,236,406 | 12/1980 | Reed et al. | 73/597 |
| 4,522,068 | 6/1985 | Smith | 73/32 A |

FOREIGN PATENT DOCUMENTS

WO87/02770 5/1987 PCT Int'l Appl. ................. 73/32 A

Primary Examiner—Hezron E. Williams
Assistant Examiner—Louis M. Arana
Attorney, Agent, or Firm—Ratner & Prestia

[57] ABSTRACT

Solute concentration measurement apparatus comprises a container (1) for a solution together with an ultrasonic transmitter (2) and receiver (3). A signal from the transmitter (2) passes through the solution to be detected by the receiver (3). A clock (5) and microprocessor (6) determine the speed of sound in the solution and hence the concentration of solute present.

11 Claims, 13 Drawing Sheets

SOLUTE CONCENTRATION MEASUREMENT APPARATUS

This application is a continuation of application Ser. No. 010,522, filed 02/03/87, now abandoned.

This invention relates to solute concentration measurement apparatus.

BACKGROUND OF THE INVENTION

In industry, and in particular in the brewing, distilling and soft drinks industries, the progress of a particular process taking place in a solution is often monitored by measuring the concentration of a solute, for example ethanol, in the solution.

At present, in order to measure the concentration of a solute in a solution a sample of the solution must be taken and analysed. Thus, close monitoring of a process requires samples to be taken at regular intervals. Sampling is time consuming and in many circumstances it is inconvenient to remove samples from solutions while the process is taking place.

SUMMARY OF THE INVENTION

According to the present invention there is provided solute concentration measurement apparatus comprising a container for receiving a solution, an ultrasonic transmitter, and an ultrasonic receiver, the transmitter and the receiver being mounted on the walls of the container such that a signal from the transmitter traverses a solution in the container to be detected by the receiver, means being provided to measure a time interval between transmission and detection of a signal.

Preferably, the container is provided with two opposing parallel walls. The ultrasonic transmitter and the ultrasonic receiver may be mounted adjacent one another on one of said walls such that the receiver detects a signal from the transmitter that has been reflected from said opposite wall. As well as giving an increased signal path length the detection of a reflected signal allows measurement to be taken in a moving stream of solution, as the reflection allows any velocity effects, caused by the movement of the solution, to be cancelled out. Alternatively the transmitter and the receiver may be each mounted on opposing walls.

Preferably also, the container is in the form of a length of tube. An inlet and an outlet may be provided at opposite ends of the tube. The tube may be inclined to ensure the discharge of air locks.

Preferably also, the signal from the transmitter is in the form of a pulse of ultrasound and is generated by the application of a voltage step to a crystal in the transmitter.

Preferably also, the clock means is in the form of a 20 mHertz clock.

Further according to the present invention there is provided a method of measuring the concentration of a solute in a solution comprising measuring the time taken for an ultrasound signal to pass through a solution over a known path length and calculating the speed of sound in the solution from the measurements.

The speed of sound in a liquid is affected by the concentration of solute present in the liquid and by finding the speed of sound in the solution the concentration of a solute present may be found.

Embodiments of the present invention will now be described by way of example, with reference to the accompanying drawings, in which.

DESCRIPTION OF SPECIFIC EMBODIMENTS

Referring to FIGS. 1 to 4 of the drawings solute concentration measurement apparatus comprises a length of tube 1, an ultrasonic transmitter 2, an ultrasonic receiver 3, a pulse generator 4, a clock 5 and a microprocessor 6.

Figure 2:
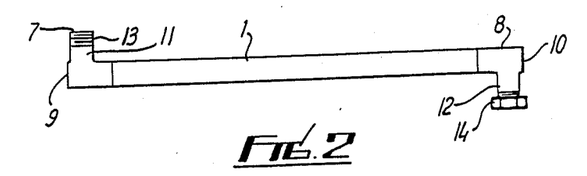
FIG. 2 is a side view of the tube of the apparatus of FIG. 1.
Figures 3, 4:
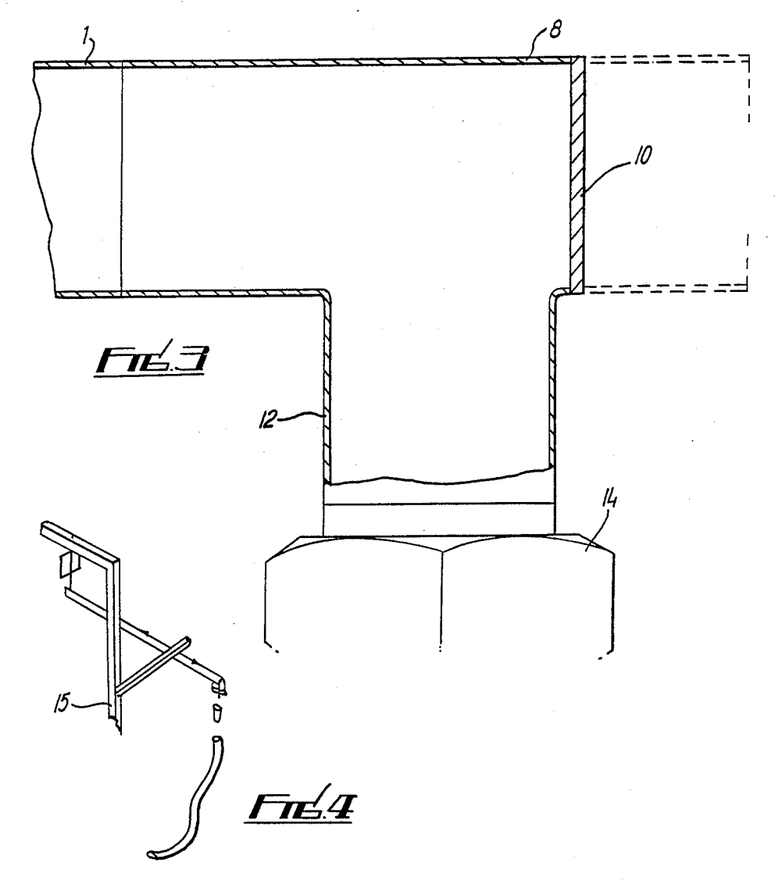
FIG. 3 is a fragmented sectional view of an end portion of the tube of FIG. 2.
FIG. 4 is a perspective view of apparatus for mounting the tube of FIG. 2.

The opposite end portions of the tube 1 are each provided with an inlet portion 7 and outlet portion 8. The portions 7 and 8 are welded to the ends of the tube 1 and have end plates 9 and 10 which are perpendicular to the central axis of the tube 1.

The portions 7 and 8 are formed from tee junctions which have had one branch of the "T" cut away and the end plates 9 and 10 welded over the cut ends.

The connecting branches 11 and 12 of the portions 7 and 8 are provided with screw threads 13 for connection by means of nuts 14 to up and downstream pipework.

In one embodiment the tube 1 is mounted on a mild steel frame 15. The inlet portion 7 of the tube 1 is connected to an existing pipe via a vertical spacer pipe. The spacer pipe ensures the tube is flooded when flow through the tube 1 is stopped.

The tube 1 is inclined at an angle of five degrees to the horizontal in the direction of fluid flow to ensure the discharge of air locks.

The outlet portion 8 of the tube 1 is connected to a hose which leads to a tank inlet.

The ultrasonic transmitter 2 and the ultrasonic receiver 3 are encased in metal cylinders and are attached to the outer face of the end plate 10 of the outlet portion 8 by means of sound conducting paste.

Figure 1:
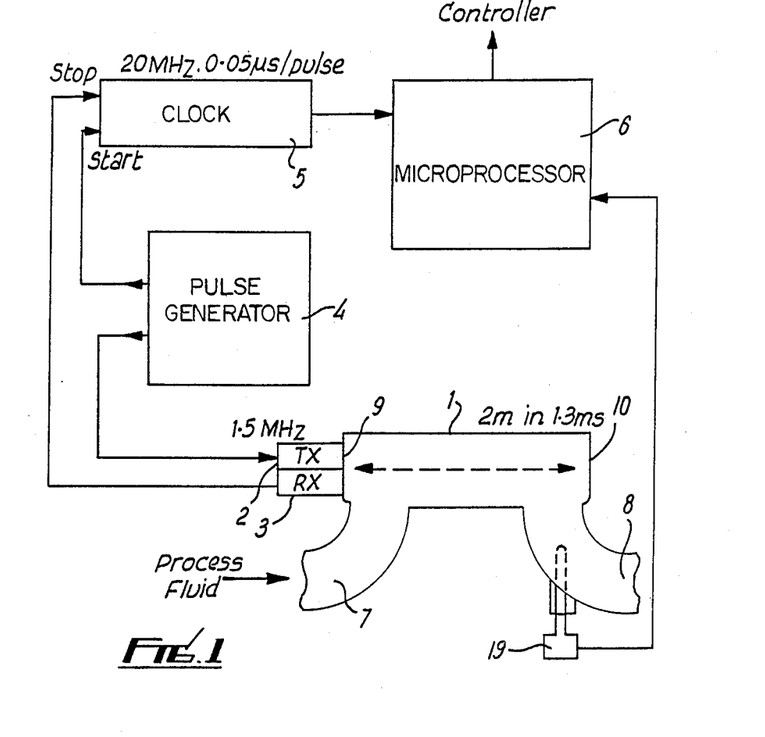
FIG. 1 is a schematic representation of solute concentration apparatus in accordance with the present invention.

When a pulse of ultrasound, at 1.5 mHertz, is generated by the application of a voltage step from the pulse generator 4 to a crystal in the transmitter 2, the pulse travels through the tube 1 from the end plate 10 to be reflected by the opposite end plate 9 and then returns to the end plate 10 to be detected by the receiver 3. The time of flight is measured before the first wave crest is detected by the receiver 3, by counting the pulses of the 20 mHertz. 0.05 us/pulse clock 5. The clock 5 is started by a signal from the pulse generator 4 and is stopped by a signal from the receiver 3. A signal from the clock 5 passes to a microprocessor 6 where the signal is converted to a velocity.

Figure 5:
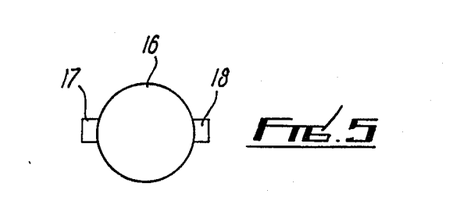
FIG. 5 is a representation of an alternative position of the ultrasonic transmitter and receiver of the apparatus of FIG. 1.

FIG. 5 of the drawings show an alternative arrangement on a tube 16 for the location of a transmitter 17 and receiver 18. This arrangement may be used when it is inconvenient to provide a tube 1 as described above. The transmitter and receiver may also be located on the same side of the tube and the ultrasonic pulse reflected from the opposite face of the tube, the path length of the pipe being twice the pipe diameter.

The velocity of sound in a liquid is affected by the concentration of solute present and in the embodiments described the measured sound velocity is used to determine the concentration of sucrose and ethanol in solutions.

Figure 6:
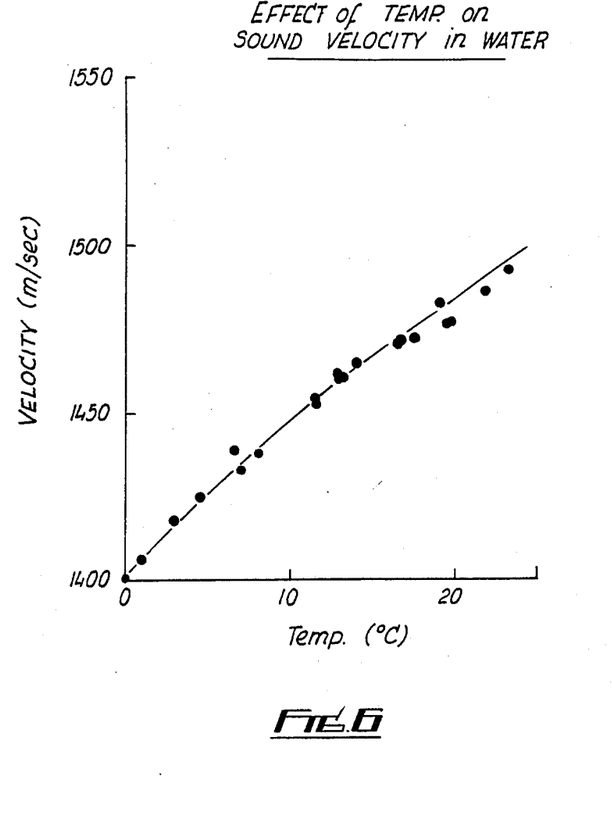
FIG. 6 is a graph showing the effect of temperature on sound velocity in water.
Figure 7:
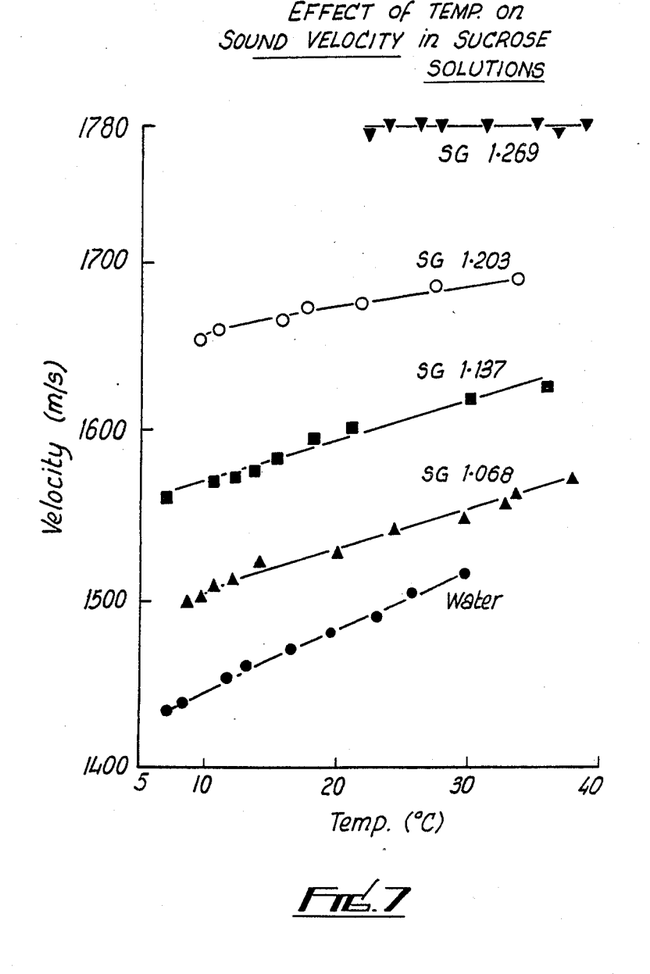
FIG. 7 is a graph showing the effect of temperature on sound velocity in sucrose solutions.

The velocity of sound in a liquid is also affected by temperature, FIGS. 6 and 7 showing graphs which illustrate the effect of temperature in water and in sucrose solutions.

If the information shown in the graphs of FIGS. 6 or 7 is held in the microprocessor 6 the apparatus may be used to measure the temperature of water or sucrose solutions. Additionally by linking the microprocessor 6 to a controller (not shown) which operates a heating-/cooling system the apparatus may be used as a temperature control.

If it is desired to measure the sucrose concentration in a carbonated for example a soft drink solution using the apparatus it is necessary to compensate for the effects of temperature and carbon dioxide ($CO_2$) on the sound velocity. By providing a temperature sensor such as a thermometer 19, in the tube 1 a signal is passed to the microprocessor 6, which is provided with look-up tables or the like, which interprets the signals from the clock 5 accordingly. A non-sampling $CO_2$ level sensor is provided and the signals from the sensor are also passed to the microprocessor 6 to be taken into account.

Figures 8, 9:
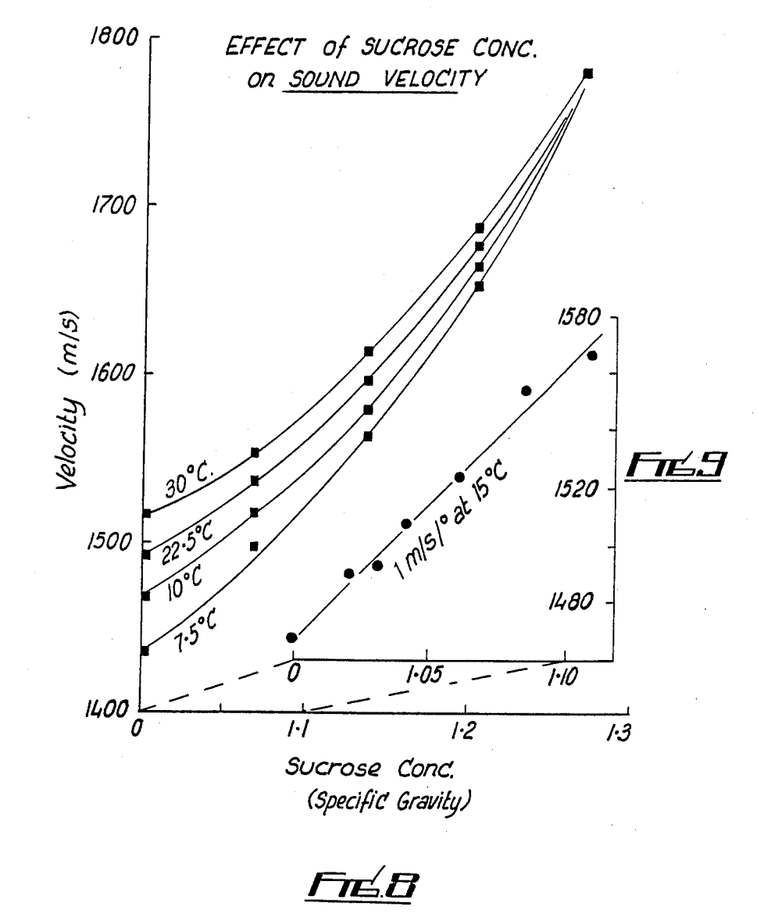
FIG. 8 is a graph showing the effect of sucrose concentration on sound velocity.
FIG. 9 is an enlarged portion of the graph of FIG. 8.

The graph of FIG. 9 illustrates the range of sucrose concentration of interest to soft drinks manufacturers over which the sound velocity is generally proportional to the density of the solution. Over a greater range, as illustrated in the graph of FIG. 8, the sound velocity is proportional to the density and the compressibility or bulk modulus of the solution. In this apparatus a timing accuracy of ±0.05 us in 1.3 ms gives an error of ±0.05'.

Figures 10, 11:
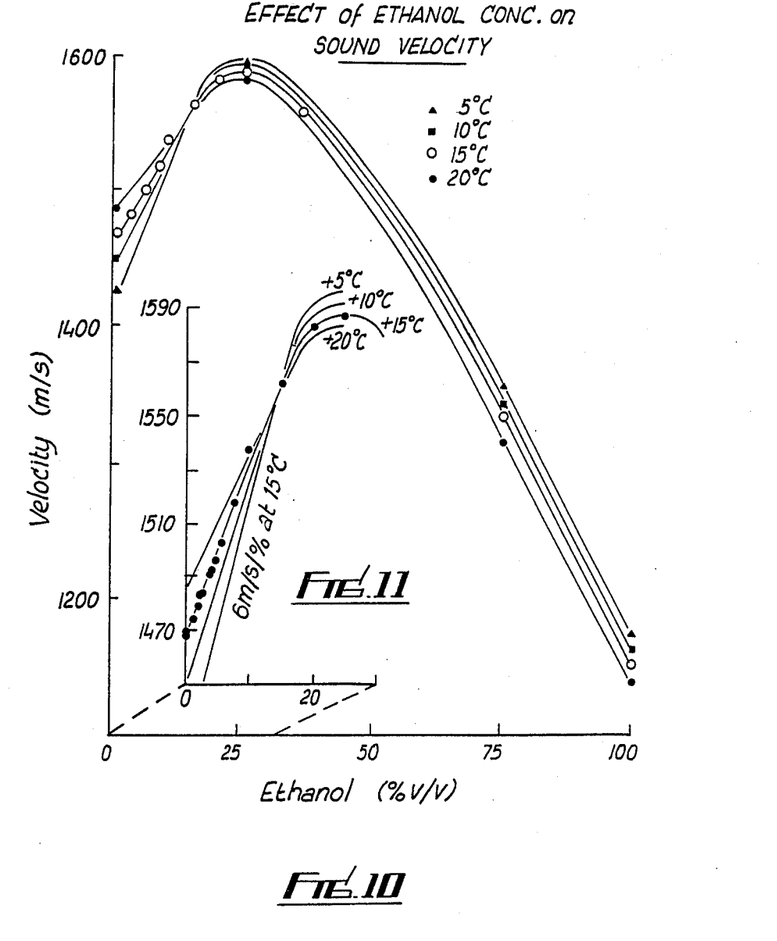
FIG. 10 is a graph showing the effect of ethanol concentration on sound velocity.
FIG. 11 is an enlarged portion of the graph of FIG. 10.

FIGS. 10 and 11 of the drawings show graphs which illustrate the change in sound velocity with the change in concentration of ethanol. There is a linear increase in sound velocity in the ethanol range of interest to brewing, which is up to 10% V/V, giving a useful linear range up to approximately 20% V/V. Beyond this concentration the velocity decreases. However, this need not detract from the usefulness of the system as it is known that in brewing the alcohol concentration will never rise above 20% V/V. Conversely useful measurements can be obtained if it is known that the alcohol content will never fall below approximately 30% V/V as is the case in the spirits industries. Using this apparatus a timing accuracy of ±0.05 ms gives an error of ±0.01%.

Figure 12:
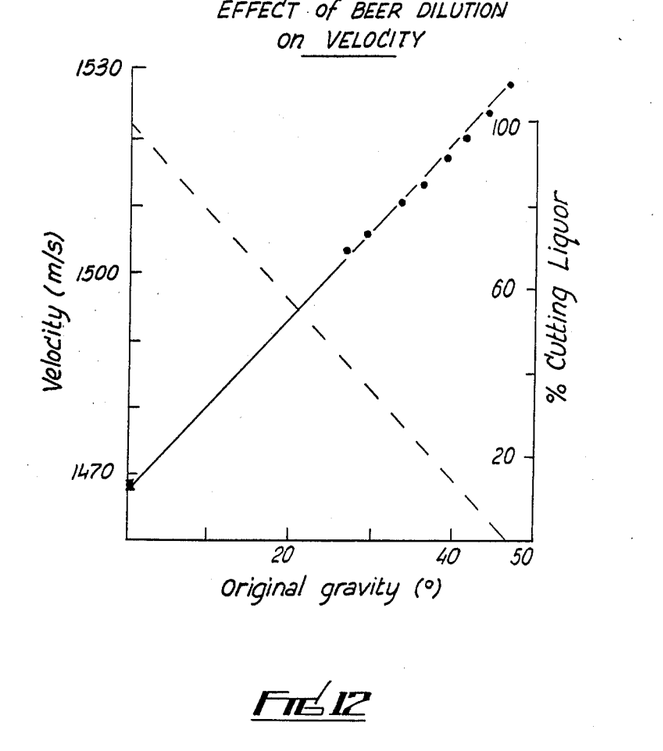
FIG. 12 is a graph showing the effect of beer dilution on sound velocity.

In brewing much of the beer sold is produced by the dilution of high strength beers. This dilution is achieved by adding "cutting liquor" to the high strength beer and the effect of dilution on sound velocity is illustrated in FIG. 12 of the drawings. If the strength or gravity of the beer prior to dilution is known, it is possible by using the apparatus to monitor the sound velocity after dilution, and determine whether the diluted beer is of correct strength.

Figure 18:
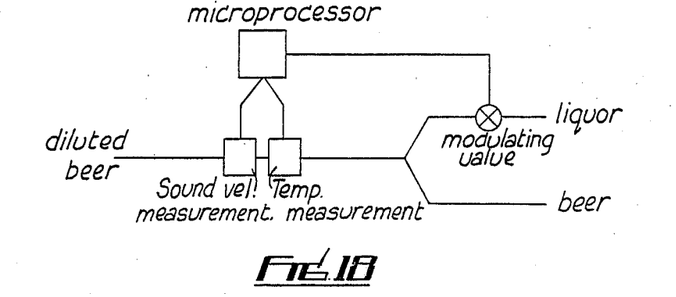
FIG. 18 is a schematic representation of an automatic dilution system where the strength of the pre-dilution beer is known.

If the measured value of dilution calculated from the sound velocity is compared with a target value set within the microprocessor a correcting signal is generated to alter the setting of the modulating value controlling the amount of cutting liquor being added to achieve the desired value. In this way, an automatic system for the dilution of highgravity beer is provided using the apparatus as illustrated in FIG. 18.

If desired, the apparatus provides a digital read out every three seconds.

Figure 13:
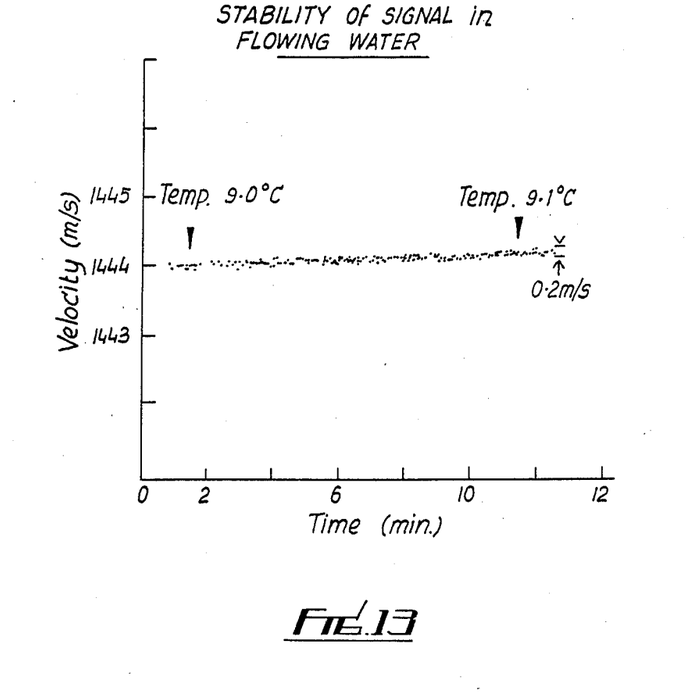
FIG. 13 is a graph showing the stability of an ultrasonic signal in flowing water.

The variation in the measured sound velocity in flowing water, as illustrated in FIG. 13 of the drawings, is ±0.1 m/s and thus beer dilution can be determined to within ±0.1'.

Where the strength or gravity prior to dilution is not known, or where it is likely to vary from a known value during the dilution process, the apparatus can be further amended to measure the strength either before or after dilution.

Figure 14:
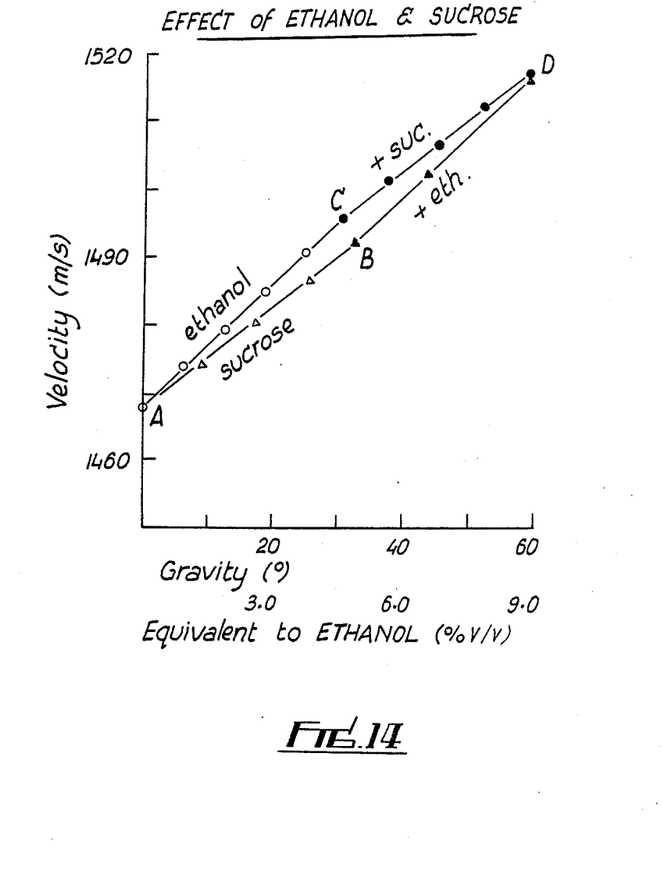
FIG. 14 is a graph showing the effect of ethanol and sucrose concentration on sound velocity.

FIG. 14 of the drawings shows a graph which illustrates the increase in sound velocity in a solution in relation to the increase in concentration of sucrose, shown by lines AB and CD, and in relation to the increase in concentration of ethanol, shown by lines AC and BD.

Point D represents a mixture of ethanol and sucrose reached either by addition of sucrose then ethanol, represented by line A B D, or by ethanol then sucrose, represented by line A C D, thus illustrating that the effect of increased concentrations of sucrose and ethanol is additive in the range of interest to brewing.

This method may therefore be used to determine the original gravity of a solution undergoing fermentation. The original gravity (O.G.) of a solution is the density, or gravity of a solution to be fermented, known as the wort, before the fermentation process has begun. The present gravity, (P.G) is the density of a solution as measured. If an independent measure of the soluble solids and ethanol concentration in the solution, that is the present gravity, is made using, for example, a densitometer, and the sound velocity is measured and corrected to a value at a temperature of 15° C. the original gravity may be found by using the equation: O.G = 0.952 (velocity at 15° C.+0.25P.G.−1467)

Figure 19:
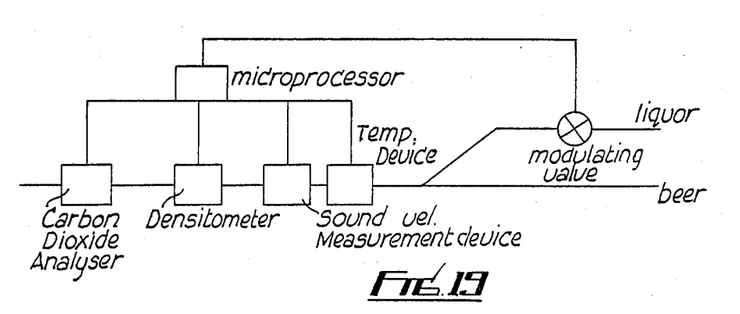
FIG. 19 is a schematic representation of an automatic dilution system where the strength of the pre-dilution beer is unknown or variable.

Using the arrangement shown in FIG. 19, the sound velocity, temperature and density, or P.G. as measured by the apparatus and the densitometer respectively are read by the microprocessor. The carbon dioxide present must also be measured using a suitable in-line instrument in order to correct the density measurement to attain the overall accuracy required for brewing purposes. These values are then calculated by the microprocessor using the equation stated above and the O.G.

The expected error for this calculation is in the region of ±0.3′ through a combination of the errors in timing and present gravity.

Figure 15:
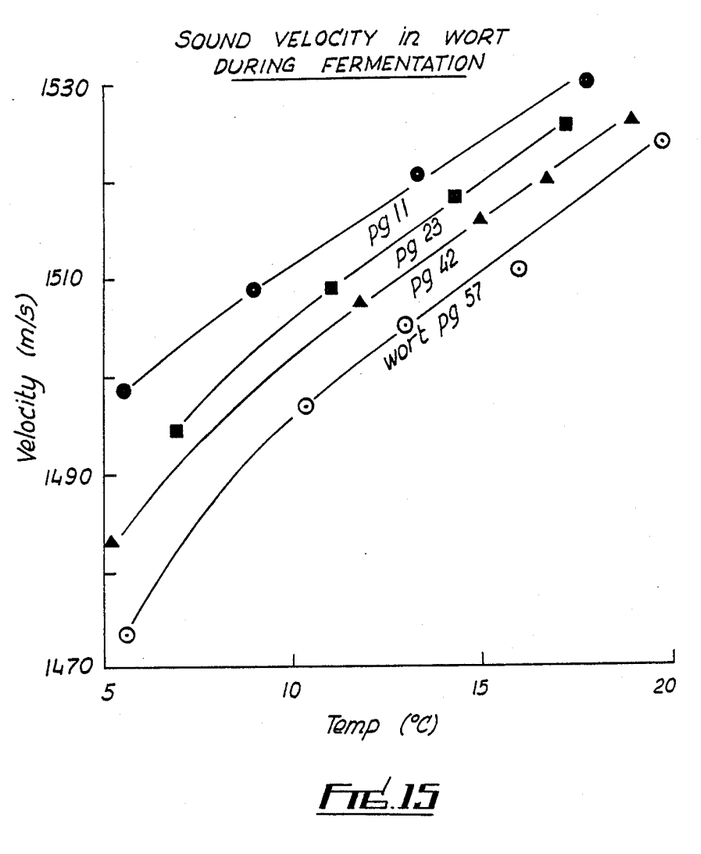
FIG. 15 is a graph showing the effect of sound velocity in wort during fermentation.
Figure 16:
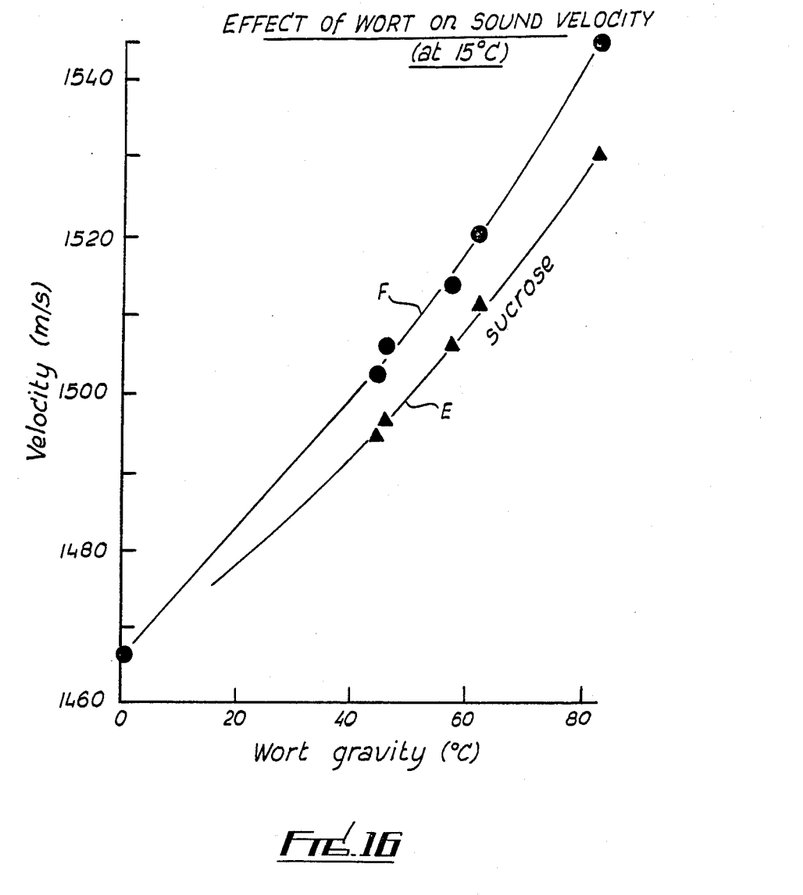
FIG. 16 is a graph showing the effect of wort on sound velocity.

FIGS. 15 and 16 of the drawings illustrate the increase in sound velocity in wort during fermentation. In FIG. 16 line E shows the increase in sound velocity as the wort gravity increases, a greater wort gravity indicating a greater concentration of sucrose in solution. Line F shows the sound velocity in the wort after fermentation, that is the sucrose originally present in the wort has been converted to ethanol. This is also illustrated in FIG. 15 where a decrease in the present gravity of the wort during fermentation, corresponding in a decrease in density as sucrose is converted to ethanol, leads to an increase in the sound velocity.

Figure 17:
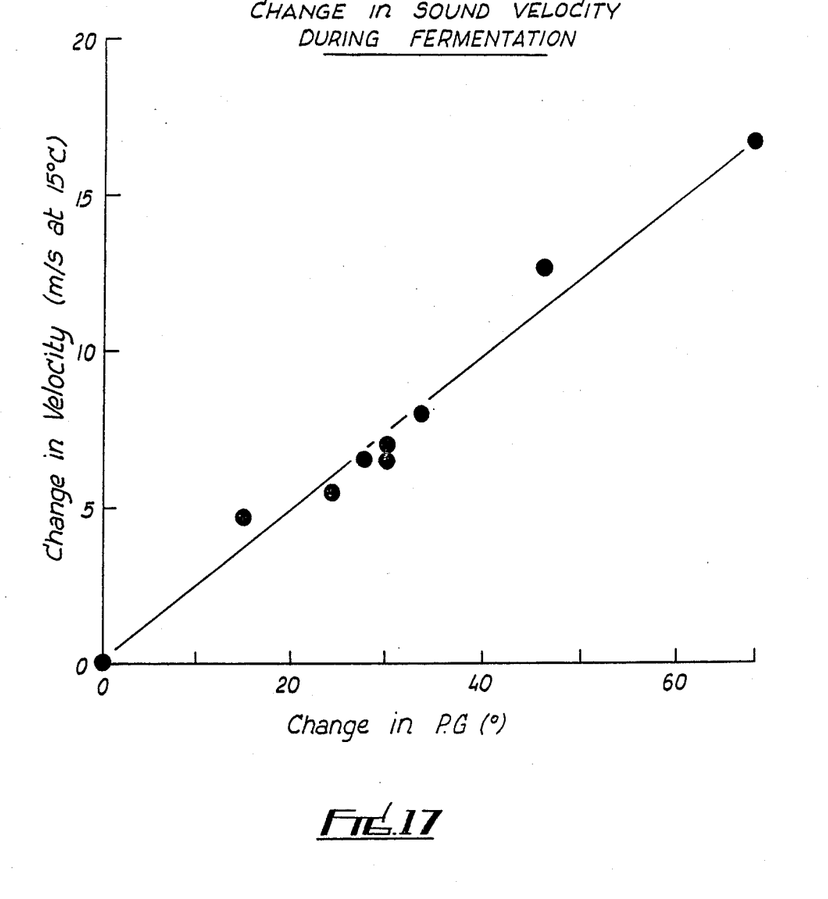
FIG. 17 is a graph showing the change in sound velocity during fermentation.

FIG. 17 of the drawings illustrates the change in sound velocity during a fermentation. The apparatus can be used to monitor this change and may provide information on the stage of fermentation and may act as a guide to indicate when the fermentation should be stopped by cooling the fermentation vessel.

Figure 20:
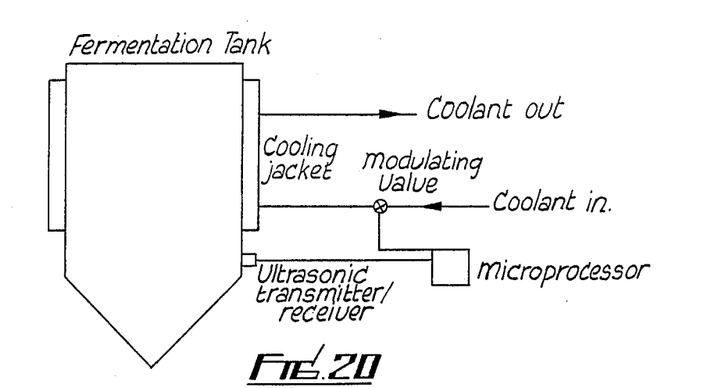
FIG. 20 is a schematic representation of a fermentation tank provided with fermentation control apparatus.

In this case, the parallel walled container described above may be a fermenting tank and the ultrasound transmitter and receiver are mounted either on opposing walls or adjacent with the signal being reflected from the opposite wall as is shown in FIG. 20. Control of the progress of the fermentation can be exercised by linking the microprocessor measuring the sound velocity, and calculating the density or P.G. of the fermenting solution, to a modulating value controlling the flow of coolant to the cooling jacket of the fermenter.

The desired profile of the fermentation is stored within the microprocessor memory in the form of a series of predetermined time related P.G. values. By comparing the actual P.G. measured using the apparatus at a particular time after the start of fermentation, with the values held in the microprocessor memory, the speed or profile of the fermentation can be controlled to the desired profile by increasing or decreasing the temperature of the fermentation solution through adjustment of the flow of coolant to the cooling jacket via the modulating value.

Small gas bubbles in solution do not effect the results obtained with the apparatus as the ultrasonic signal have a relatively large wavelength (>15 mm) compared to the diameter of the bubbles. Thus the solute concentration measurement apparatus may be used to measure the temperature of a solution, to measure solute concentration, for the monitoring and control of dilution systems, to provide an absolute calibration and to monitor the progress of processes involving the transformation of solutes.

Additionally the apparatus provides means for hygenic analysis as the apparatus can be fitted in line thus avoiding sampling and intrusion.

Modifications and improvements may be made without departing from the scope of the invention.

What is claimed is:

1. A method for measuring the original gravity of a liquid comprising the steps of:
   measuring the velocity of sound through the liquid;
   measuring the present gravity of the liquid; and calculating from these two measurements the original gravity using the equation:

$$O.G. = a[v + b(P.G.) - c]$$

where
   O.G. is the original gravity,
   P.G. is the present gravity,
   v is the velocity of sound at 15° C. and;
   a, b, c are empirical constants.

2. A method as claimed in claim 1, wherein the liquid is beer and the present gravity is a measure of the soluble solids and ethanol concentration in the beer.

3. A method as claimed in claim 1, wherein the present gravity is measured using a densitometer.

4. A method as claimed in claim 1, wherein the velocity of sound is measured by measuring the time taken for an ultrasound signal to traverse the liquid over a known path length.

5. A method as claimed in claim 1, wherein the sound velocity measurement is corrected for temperature.

6. A method as claimed in claim 2 and including the steps of measuring the carbon dioxide in the liquid and correcting the present gravity measurement as a function of the carbon dioxide measurement.

7. Apparatus for measuring the original gravity of a liquid comprising means for measuring the velocity of sound in the liquid, means for measuring the present gravity of the liquid and means for evaluating the original gravity from the sound velocity measurement and the present gravity measurement, said means for evaluating using the equation:

$$O.G. = a[v + b(P.G.) - c]$$

where
   O.G. is the original gravity,
   P.G. is the present gravity,
   v is the velocity of sound at 15° C. and;
   a, b, c are empirical constants.

8. Apparatus as claimed in claim 7, wherein the means for measuring the sound velocity comprises a container for receiving a solution, an ultrasonic transmitter, and an ultrasonic receiver, the transmitter and receiver being mounted on the walls of the container such that a signal from the transmitter traverses a solution in the container to be detected by the receiver, means being provided to measure a time interval between transmission and detection of a signal.

9. Apparatus as claimed in claim 7, wherein the present gravity measurement means is a densitometer.

10. Apparatus as claimed in claim 7 and including means for correcting the sound velocity measurement for temperature.

11. Apparatus as claimed in claim 7 and including means for determining the carbon dioxide dissolved in the liquid and for correcting the present gravity measurement as a function of the carbon dioxide measurement.

* * * * *